United States Patent
Cheiky et al.

(10) Patent No.: US 8,835,517 B2
(45) Date of Patent: Sep. 16, 2014

(54) METHOD FOR PRODUCING DIMETHYL ETHER USING A SEPARATOR

(75) Inventors: Michael Cheiky, Thousand Oaks, CA (US); James Hillier, Camarillo, CA (US)

(73) Assignee: Cool Planet Energy Systems, Inc., Camarillo, CA (US)

( * ) Notice: Subject to any disclaimer, the term of this patent is extended or adjusted under 35 U.S.C. 154(b) by 126 days.

(21) Appl. No.: 13/484,082

(22) Filed: May 30, 2012

(65) Prior Publication Data

US 2013/0324622 A1   Dec. 5, 2013

(51) Int. Cl.
C07C 27/00 (2006.01)
C07C 41/01 (2006.01)
C07C 41/42 (2006.01)

(52) U.S. Cl.
CPC ............. *C07C 41/01* (2013.01); *C07C 41/42* (2013.01)
USPC .......................................................... 518/700

(58) Field of Classification Search
USPC .......................................................... 518/700
See application file for complete search history.

(56) References Cited

U.S. PATENT DOCUMENTS

| | | | |
|---|---|---|---|
| 2,162,838 A * | 6/1939 | Cole et al. ................. | 423/234 |
| 6,147,125 A | 11/2000 | Shikada et al. | |
| 6,458,856 B1 | 10/2002 | Peng et al. | |
| 7,910,630 B2 | 3/2011 | Rostrup-Nielsen et al. | |
| 2008/0182912 A1 | 7/2008 | Van Den Berg et al. | |
| 2010/0216897 A1 | 8/2010 | Rostrup-Nielsen | |
| 2010/0305220 A1 | 12/2010 | Kukkonen et al. | |

FOREIGN PATENT DOCUMENTS

CN   1085824 A   4/1997

OTHER PUBLICATIONS

International Search Report and Written Opinion issued by the U.S. Patent and Trademark Office as the International Searching Authority for corresponding International Application No. PCT/US2013/042302 mailed Nov. 7, 2013 (7 pgs.).

* cited by examiner

*Primary Examiner* — Jafar Parsa

(74) *Attorney, Agent, or Firm* — Wilmer Cutler Pickering Hale and Dorr LLP

(57) ABSTRACT

A method for the production of dimethyl ether is disclosed which utilizes: a dimethyl ether synthesis catalyst that converts synthesis gas to a dimethyl ether containing stream, wherein the dimethyl ether containing stream is directed to an absorption column containing water as a scrubbing agent and operating in a temperature range from 1° C.-20° C. and pressure range from 20 psig to 500 psig, and wherein the scrubbing liquid resulting from the exposure of the dimethyl ether containing stream to the absorption column is directed to a flash evaporation unit operating at 25° C.-100° C. and pressure range −15 psig to 15 psig to produce a product stream rich in dimethyl ether.

10 Claims, 2 Drawing Sheets

METHOD FOR PRODUCING DIMETHYL ETHER USING A SEPARATOR

FIELD OF THE INVENTION

The invention broadly relates to synthesis gas applications, and more particularly to a method for the production of dimethyl ether from synthesis gas using a novel separation technology.

BACKGROUND OF THE INVENTION

Dimethyl ether (DME) is a versatile compound capable of being used as combustion fuel, cooking fuel, additive to liquefied propane gas, and intermediate for the production of other chemical compounds. The basic steps in the dimethyl ether synthesis from synthesis gas are as are as follows:

$$CO + 2H_2 \rightarrow CH_3OH \quad 1)$$

$$2CH_3OH \rightarrow CH_3OCH_3 + H_2O \quad 2)$$

Equilibrium conversion may be increased if the water gas shift reaction (WGS) is also involved:

$$CO + H_2O \rightarrow CO_2 + H_2$$

In this case the net reaction is:

$$3CO + 3H_2 \rightarrow CH_3OCH_3 + CO_2$$

Dimethyl ether is produced industrially in a one step process in which the methanol synthesis, dehydration, and WGS steps are performed on the same catalyst bed reactor, or in a two step process in which the two or more steps are performed in two or more sequential reactors. The one-step process is preferable for thermodynamic and economic considerations. This process is known as the syngas-to-DME process. The reaction is favored by high pressures and low temperatures. In both processes carbon dioxide is produced in stoichiometric amounts along with dimethyl ether. A prevalent problem in dimethyl ether synthesis from synthesis gas is the selective separation of the reaction product from carbon dioxide, methanol, water and unreacted syngas.

Prior art technology for the separation of dimethyl ether from other products includes U.S. Patent Application No. 2010/0216897 titled "Process for the preparation of Dimethyl Ether", which discloses a 2-stage scrubbing process that uses DME in a first zone and methanol in a second zone as solvents. The physical basis for the invention lies in the high solubility of carbon dioxide in DME, and the high solubility of DME in methanol. Dimethyl ether, methanol and water are condensed out of the initial gas stream while allowing the flow of carbon dioxide and unreacted synthesis gas. The carbon dioxide (still containing DME vapor due to the high solubility of $CO_2$ in DME) is passed through a first DME-containing scrubbing unit which removes carbon dioxide. Subsequently the $CO_2$-reduced stream is passed through a second unit containing methanol which removes remnant DME. Unreacted synthesis gas is sent back to the DME synthesis reactor.

U.S. Pat. No. 7,910,630 assigned to Haldor Topsoe discloses a separation method which utilizes a cooled solvent of a dialkyl ether of a polyethylene glycol to solubilize both carbon dioxide and DME after an initial condensation of methanol and water. The remaining $CO_2$ and DME are selectively desorbed in a subsequent process. U.S. Pat. No. 7,652,176, also to Haldor Topsoe, discloses passing a product stream comprised of DME, methanol, $CO_2$, and unreacted synthesis gas through an absorber comprised of 20-40% potassium carbonate to reduce the carbon dioxide levels below 500 ppm. An additional solid adsorbent comprised of zeolites, molecular sieves, or activated aluminas are used to bring down the levels below 1 ppm. Subsequent exposure to a distillation column affords a separation of the DME from the methanol/water mixture.

U.S. Pat. No. 6,458,856 assigned to Air Products, Inc. describes a scrubbing solvent that uses a mixture of dimethyl ether and methanol to separate $DME/CO_2$ from unreacted synthesis gas after an initial condensation of water and carbon dioxide. The $DME/CO_2$ mixture is subsequently flash vaporized and distilled. This mixture is said to be superior to scrubbing agents of pure water, pure methanol, or pure DME because of the high solubility of $CO_2$ in the mixture and low vapor pressure of the mixture. U.S. Pat. No. 5,908,963 assigned to Haldor Topsoe discloses a separation of $CO_2$/unreacted syngas from dimethyl ether, methanol and water via condensation. Methanol is then distilled out from the condensed mixture and recycled to be utilized as a DME scrubber.

U.S. Pat. No. 6,147,125 to Shikada et al. discloses a separation method which condenses methanol and water first, and passes through dimethyl ether, carbon dioxide, and unreacted synthesis gas. The syngas is recycled, while the $DME/CO_2$ mixture is condensed out. A subsequent distillation separates the dimethyl ether form the carbon dioxide.

Chinese Patent No. 1085824A teaches the use of water or ethanol as scrubber solvent in the production of dimethyl ether from synthesis gas. Extraction conditions are said to be room temperature and pressure above 10 bar, with a volume ratio >=0.03 when water is used as an extractant and >=0.01 when ethanol is used as the extractant. Han et at (Chemical Industry and Engineering Progress, 2008-06) in an article titled "Separation process of dimethyl ether synthesized by one-step method from syngas" describe a separation process that utilizes an absorption column at 40° C. and 20 bar and that contains de-ionized water as the scrubbing solvent. The process is said to produce high purity DME after a large number of refluxes.

SUMMARY OF THE INVENTION

Embodiments of the invention relate to a process that entails the catalytic production of dimethyl ether from synthesis gas to dimethyl ether, whereby the product mixture comprising dimethyl ether, methanol, carbon dioxide and water, and unreacted synthesis gas is subsequently separated into two streams. Specifically, one stream primarily comprises dimethyl ether and carbon dioxide, and the other stream comprises unreacted synthesis gas, carbon dioxide, methanol and water. Embodiments of the invention involve chilling the product mixture to a temperature of 1-20° C. under high pressure prior to introduction to a water-based absorption column, separating a gaseous effluent consisting of unreacted synthesis gas, water, methanol, and small quantities of carbon dioxide and dimethyl ether, from a water-based solution containing dimethyl ether and carbon dioxide, and heating the solution to a temperature between 25-100° C. in a low pressure environment to flash evaporate the carbon dioxide and dimethyl ether. This process represents an inexpensive and relatively rapid method for the separation of diethyl ether from the product stream.

One embodiment of the invention is directed toward a method for the production of dimethyl ether comprising: a dimethyl ether synthesis catalyst to convert synthesis gas to a dimethyl ether containing stream; wherein the dimethyl ether containing stream is exposed to an absorption column containing water as a scrubbing agent and operating in a temperature range from 1° C. to 20° C. and pressure range from 20 psig to 500 psig, thereby resulting in a scrubbing liquid; wherein the scrubbing liquid resulting from the exposure of the dimethyl ether containing stream to the absorption column is directed to a flash evaporation unit operating in a temperature range from 25° C. to 100° C. and pressure range from −15 psig to 15 psig to produce a product stream rich in dimethyl ether.

In one implementation of the above method, the product stream contains more than 50% dimethyl ether by volume. In a further implementation, the product stream contains more than 60% dimethyl ether by volume. In yet another implementation, the product stream contains more than 70% dimethyl ether by volume. Additionally, the absorption column can be selected from the group consisting of: counter-current spray towers, counter-current packed-bed absorbers, cross-flow scrubbers, and tray-tower absorbers. In some cases, the absorption column may comprise at least one packed tower comprising high surface packing material.

In some implementations of the above method, the dimethyl ether containing stream also contains one or more of carbon dioxide, carbon monoxide, hydrogen, methane, ethane, propane, methanol, and water. In addition, the absorption column may selectively absorb dimethyl ether and carbon dioxide from the dimethyl ether containing stream. The scrubbing agent, absorbed dimethyl ether and absorbed carbon dioxide water solution may be flash evaporated under vacuum. Additionally, the scrubbing liquid can be preheated prior to introduction to the flash evaporation unit.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Dimethyl ether (DME) has a nominal boiling point of −24.6° C. The solubility of dimethyl ether in water at room temperature has been reported as 0.027 on a mole fraction basis. At high temperatures this fraction is expected to decrease, and higher pressures will increase it. At 3.1 bar and 50° C., the experimental equilibrium mole fraction is 0.028 and at 10.2 bar and 50° C., the mole fraction increases to 0.155 (J. Chem. Data 1984, vol. 29, pp. 324-329). The prior art does not teach or suggest a separation method that comprises exposing a DME stream resulting from a DME synthesis process to a scrubbing process that uses low-temperature water followed by flash evaporation of the scrubbing solvent and DME.

Embodiments of the present invention involve a method for the production of dimethyl ether that includes the following steps: 1) conversion of synthesis gas to dimethyl ether, 2) exposure of product stream to a low temperature high pressure water-containing absorption column to scrub carbon dioxide and dimethyl ether, and 3) subsequent flash evaporation of scrubbed mixture at low pressure and high temperature to effect a product rich in dimethyl ether.

Figure 1:
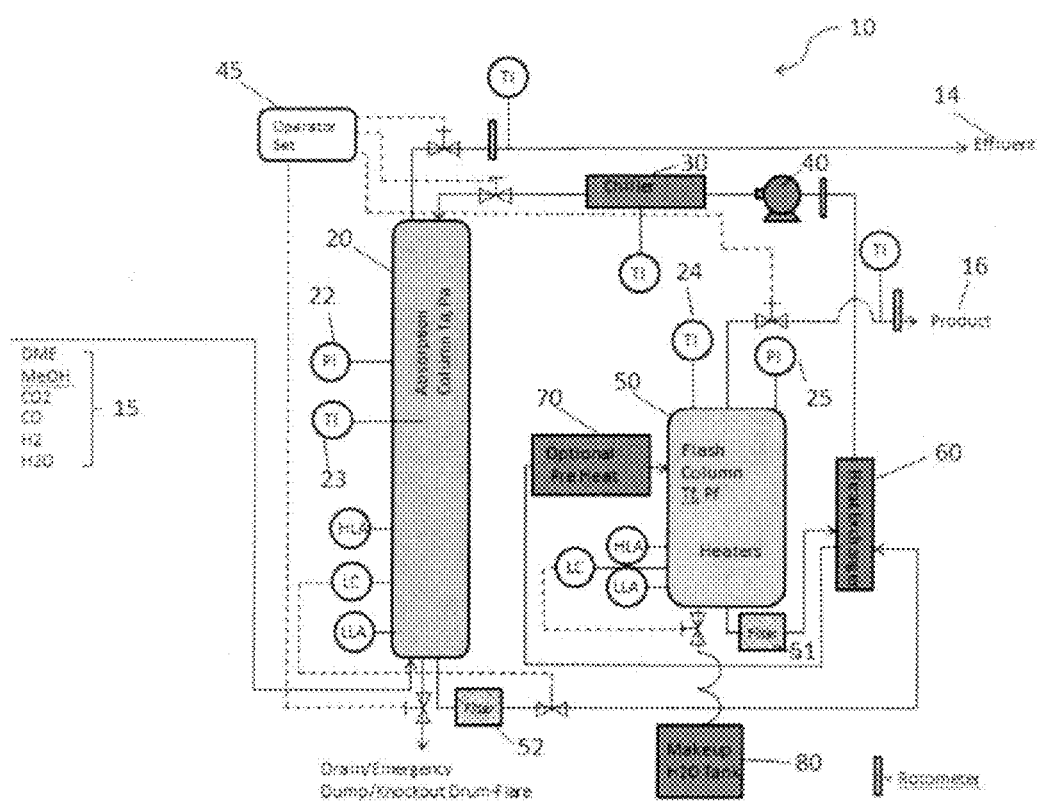
FIG. 1 is a diagram illustrating the basic principles of a process for producing dimethyl ether, in accordance with an embodiment of the present invention.

FIG. 1 is a diagram illustrating the basic principles of a process for producing dimethyl ether, in accordance with an embodiment of the present invention. Referring to FIG. 1, product mixture 15 results from the conversion of synthesis gas (CO and $H_2$) into dimethyl ether. This is typically accomplished via the use of a methanol synthesis catalyst in combination with a dehydration catalyst.

The methanol synthesis catalysts are well known and comprise co-precipitated oxides of Cu and Zn. These oxides may be co-precipitated with various oxides known to those skilled in the art, including oxides of aluminum, chromium, manganese, zirconium and boron. Typical ratios of Cu to Zn may vary from 5:1 to 1:5. In the case of an aluminum oxide, Al to Cu ratio may vary from 0.05 to 2 and Al to Zn ratio may vary from 0.1 to 1. Co-precipitation may also be performed onto a sol or onto a suspension of well dispersed solid particles. Generally co-precipitation is effected by addition of a basic salt such as sodium carbonate, sodium bicarbonate, ammonium carbonate, or ammonium hydroxide.

The dehydration catalyst serves the important role of dehydrating methanol and further pushing the equilibrium synthesis gas conversion. Well known solid acids such as silica alumina, gamma alumina, activated alumina or ZSM-5 are often used to effect this dehydration. Acidity of the catalyst is important for the dehydration reaction. If the acidity of the dehydration catalyst component is low, the resulting catalyst will exhibit low activity as it cannot convert the methanol formed to DME, thereby affecting the equilibrium synthesis gas conversion. If the acidity of the dehydration compound is high, the resulting catalyst will further dehydrate the DME formed to hydrocarbons, thus affecting the production rate of DME. The dehydration component controls the DME selectivity.

Product mixture 15 contains carbon dioxide as its primary co-product. Water from the water gas shift reaction and unreacted methanol are also minor co-products. Methane, ethane, propane, and other light hydrocarbons may also be produced, depending on catalyst conditions. Unreacted synthesis gas is also typically in the gas stream.

The product mixture 15 is fed to an absorption column 20 containing cold water at high pressures. The water scrubs out dimethyl ether and carbon dioxide, while leaving the remaining components of the product stream. The water is kept cold via chiller 30 at temperatures $T_a$ preferably in the range of 1-20° C. Colder temperatures and higher pressures increase the solubilities of dimethyl ether and carbon dioxide, and provide a better starting point for the subsequent flash evaporation. The column is pressurized to pressure. $P_a$ via compressor 40 and the pressure may vary from preferably from 20 psig to 500 psig, and most preferably from 30 psig to 400 psig. In essence, the cold temperatures and high pressures in the column in combination with subsequent high temperature low pressure flash evaporation assure a larger capacity of removed material. This represents a novel aspect of the invention. Absorption column 20 may comprise a number of well-known high surface structures designed to maximize adsorption, including counter-current spray towers, counter-current packed-bed absorbers, cross-flow scrubbers, and tray-tower absorbers. Absorption column 20 may contain any number of temperature sensors 23 and pressure sensors 22 to monitor the absorption conditions. Level sensors (shown as HLA, LC, and LLA) may also be included.

An effluent 14 comprising unreacted synthesis gas and minor components of dimethyl ether and carbon dioxide is directed for recycling, combustion, or venting. The counter flowing liquid is directed through filter 52 to heat exchanger 60 and optional preheater 70 to flash evaporation unit 50. The flash evaporation unit is held at pressure $P_r$ and temperature $T_r$. Pressure may vary from −15 psig to 15 psig and the temperature may vary from 25° C. to 100° C. Temperatures and pressures are monitored via sensors 24 and 25. Additional heaters within the unit ensure a constant temperature within the unit. Evaporated product 16 comprises primarily dimethyl ether with a minor component of carbon dioxide. In some embodiments the dimethyl ether concentration in the product stream is greater than 50%. In other embodiments it is more than 60% and in yet other embodiments, it is greater than 70%. The carbon dioxide can be sent to a carbon dioxide scrubber, or sent to a gasification or reformer unit, where it may be recycled to carbon monoxide. Water that accumulates at the bottom of the flash unit is directed to filter 51 and heat exchanger 60 back to the absorption column 20. An additional water reservoir 80 supplies needed water to keep the water at predetermined levels as monitored by water level sensors HLA, LC and LLA. All water, temperature and pressure settings can be controlled via operator control 45.

The present invention may be incorporated into any system that produces dimethyl ether, in particular systems that produce synthesis gas, such as coal gasification, natural gas wet or dry reforming, fermentation systems or biomass pyrolysis systems followed by gasification. A biomass pyrolysis system that produces DME and uses a separation method of the present invention is demonstrated in the following example.

ILLUSTRATIVE EXAMPLE 1

Figure 2:
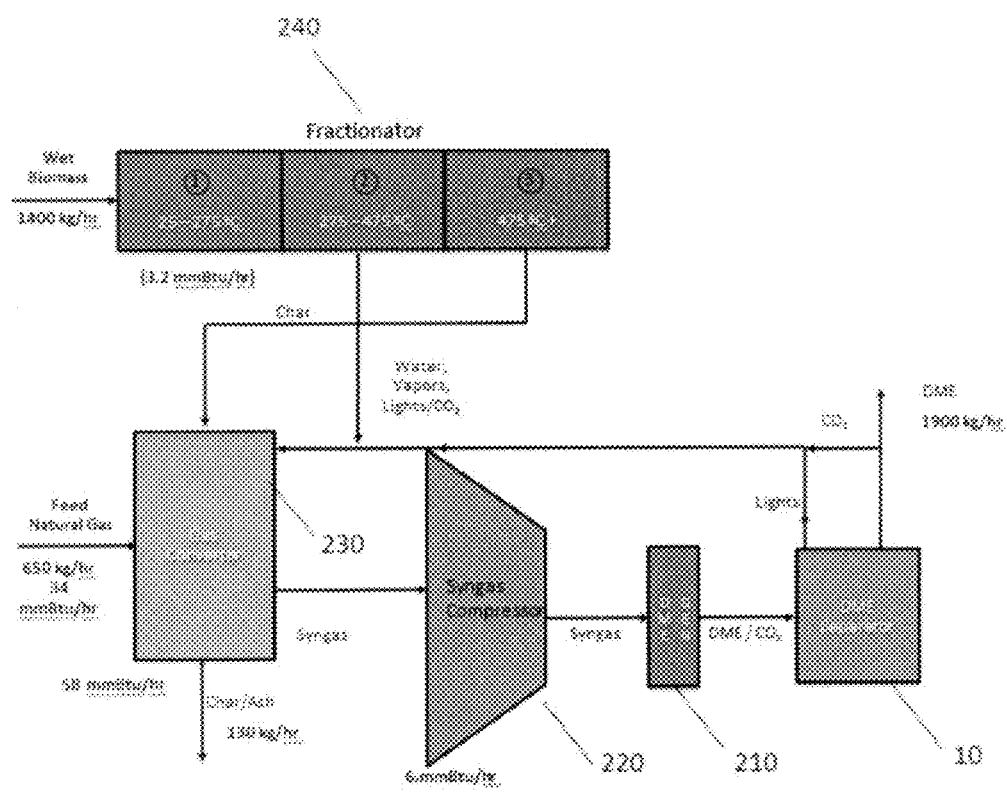
FIG. 2 is a schematic illustrating a dimethyl ether production scheme using a fractionator for biomass decomposition and a natural gas feed as additional hydrogen source, whereby the dimethyl ether is separated using a method of the present invention.

FIG. 2 is a schematic illustrating a dimethyl ether production scheme using a fractionator for biomass decomposition and a natural gas feed as additional hydrogen source, whereby the dimethyl ether is separated using a method of the present invention. In the example, 1400 kg/hr of wet biomass is introduced into a pyrolysis system 240 that selectively decomposes the biomass into different components by applying ramps of temperature and pressure shocks at a number of stations. This pyrolysis has been detailed in U.S. Pat. No. 8,173,044, the content of which is incorporated herein by reference in its entirety. FIG. 2 outlines the biomass conversion process to dimethyl ether and the separation method. Three fractionation stations are listed. The last station produces char that is fed to gas converter 230, which also receives 650 kg/hr natural gas as feedstock. Syngas produced from the gas converter is compressed via compressor 220 and fed to dimethyl synthesis reactor 210, which outputs a stream comprising 18% dimethyl ether, 26% carbon dioxide, 18% carbon monoxide, 20% hydrogen, 18% methane and less than 1% water and methanol. The absorption column in DME separator 10 operates at 10° C. and 150 psig, while the flash column operates at 40° C. and 8 psig. The effluent from the output stream is directed to gas converter 230 for recycling. Carbon dioxide from the output stream (comprised of 76% DME, 24% $CO_2$) is also directed to recycling to the gas converter. 1900 kg/hr DME exits out the system.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. A method for the production of dimethyl ether comprising:
    converting synthesis gas to a dimethyl ether containing stream using a dimethyl ether synthesis catalyst;
    exposing the dimethyl ether containing stream to an absorption column containing water as a scrubbing agent and operating in a temperature range from 1° C. to 20° C. and pressure range from 20 psig to 500 psig, thereby resulting in a scrubbing liquid; and
    directing the scrubbing liquid resulting from the exposure of the dimethyl ether containing stream to the absorption column to a flash evaporation unit operating in a temperature range from 25° C. to 100° C. and pressure range from −15 psig to 15 psig to produce a product stream rich in dimethyl ether.

2. The method of claim 1, wherein the product stream contains more than 50% dimethyl ether by volume.

3. The method of claim 1, wherein the product stream contains more than 60% dimethyl ether by volume.

4. The method of claim 1, wherein the product stream contains more than 70% dimethyl ether by volume.

5. The method of claim 1, wherein the absorption column is selected from the group consisting of: counter-current spray towers, counter-current packed-bed absorbers, cross-flow scrubbers, and tray-tower absorbers.

6. The method of claim 1, wherein the absorption column comprises at least one packed tower comprising high surface packing material.

7. The method of claim 1, wherein the dimethyl ether containing stream also contains one or more of: carbon dioxide, carbon monoxide, hydrogen, methane, ethane, propane, methanol, and water.

8. The method of claim 1, wherein the absorption column selectively absorbs dimethyl ether and carbon dioxide from the dimethyl ether containing stream.

9. The method of claim 8, wherein the scrubbing agent, absorbed dimethyl ether and absorbed carbon dioxide water solution are flash evaporated under vacuum.

10. The method of claim 1, where the scrubbing liquid is preheated prior to introduction to the flash evaporation unit.

* * * * *